United States Patent
Grams et al.

[11] Patent Number: 6,067,860
[45] Date of Patent: May 30, 2000

[54] CIRCUIT DEVICE INTEGRITY EVALUATION ARRANGEMENT AND METHOD

[75] Inventors: Michael L. Grams; Michael Chauncey Day, both of Austin, Tex.

[73] Assignee: Advanced Micro Devices, Inc., Sunnyvale, Calif.

[21] Appl. No.: 09/135,122

[22] Filed: Aug. 17, 1998

[51] Int. Cl.[7] .................................................. G01N 3/20
[52] U.S. Cl. ............................ 73/814; 73/848; 73/849
[58] Field of Search ........................ 73/810, 814, 815, 73/816, 817, 847, 848, 853, 856, 857

[56] References Cited

U.S. PATENT DOCUMENTS

| | | | |
|---|---|---|---|
| 4,282,759 | 8/1981 | Merrell | 73/827 |
| 4,292,852 | 10/1981 | Morris | 73/827 |
| 5,184,517 | 2/1993 | Kelzer | 73/851 |
| 5,447,072 | 9/1995 | Holung | 73/848 |
| 5,567,884 | 10/1996 | Dickinson et al. | 73/814 |

OTHER PUBLICATIONS

Torque Stress Analysis for Printed Circuit Boards Carrying Peripherally Leaded Modules, Peter A. Engel, IBM Corp. (No Date).

Advances in Electronic Packaging, vol. 2, American Society of Mechanical Engineers, presented at INTERpack '95, Mar. 26–30, 1995.

*Primary Examiner*—Max Noori

[57] ABSTRACT

According to one aspect of the disclosure, the present invention provides methods and arrangements for testing the integrity of laminate and solder adhesion strength in circuit devices. Methods include securely mounting one end of a circuit device, and affixing a rotatable shaft attached to a controllable servo motor to the other end of the circuit device. The circuit device is monitored so as to be able to detect failure, and torque is applied to the circuit device from the servo motor. When failure of the circuit device is detected, the torque is reduced.

20 Claims, 4 Drawing Sheets

CIRCUIT DEVICE INTEGRITY EVALUATION ARRANGEMENT AND METHOD

FIELD OF THE INVENTION

The present invention relates to equipment and methods for testing circuit device integrity, including laminate and solder adhesion strength. The present invention has particular application for plastic ball grid array (PBGA) packages and printed circuit boards (PCBs).

BACKGROUND OF THE INVENTION

The semiconductor industry has seen tremendous advances in technology in recent years which have permitted dramatic increases in circuit density and complexity, and equally dramatic decreases in power consumption and package sizes. Present semiconductor technology now permits single-chip microprocessors with many millions of transistors, operating at speeds of tens (or even hundreds) of MIPS (millions of instructions per second) to be packaged in relatively small, air-cooled semiconductor device packages. Such microprocessors are typically mounted on printed circuit boards with other components, which are coupled with the microprocessor. Adhesion of the various laminate components to the printed circuit board during its life is a major concern in quality control. Such printed circuit board packages must also necessarily contain a great number of electrical connections, which typically comprise solder joints. Solder joints are also used for reasons of mechanical integrity. Quality concerns exist concerning the printed circuit board's long term integrity regarding preconditioning, temperature cycles, and temperature/humidity stresses.

Present methods and apparatus used to test adhesion of laminate components and solder joint integrity in printed circuit board packages are expensive. Further, existing testing methods and apparatus are limited in effectiveness due to the relatively long length of time required to complete testing. Finally, concerns exist in the industry with regard to the reliability of existing testing methods.

SUMMARY OF THE INVENTION

Generally, the present invention provides methods and arrangements for testing the integrity of circuit devices such as plastic ball grid array (PBGA) packages, printed circuit boards (PCBs), and packages mounted on PCBs, such as PBGA packages, ceramic BGA packages, PQFP surface mount devices, and the like, hereinafter referred to collectively as circuit devices. Certain aspects of the invention are directed to testing the laminate and/or solder adhesion strength in such devices.

In one embodiment of the invention, a method for evaluating the integrity of a circuit device is disclosed. The method comprises stabilizing a portion of the circuit device relative to another portion of the circuit device. Another end of the circuit device is attached to a controllable motor shaft, which is connected to a servo motor. A servo controller is connected to the servo motor. Prior to testing, the circuit device is energized so as to be able to determine the moment of failure. The servo controller causes the motor shaft to rotate, which applies torque to the circuit device. When a failure condition is detected, the torque is caused to be reduced. The method can be used for cyclic testing, including testing at elevated temperature, which greatly shortens the length of time involved in testing. The cyclic nature and amount of angular displacement applied can be varied to suit individual requirements and for determination of the robustness of the PBGA device.

In a more specific embodiment, an apparatus for evaluating the integrity of a circuit device, including the evaluation of field reliability, is disclosed. Means for stabilizing a portion of a circuit device relative to another portion of a circuit device include a clamping mechanism, such as a mechanical or electromechanical vice, clamp, catch, or fastener. An assembly including a controllable motor shaft and a servo controller attaches to another portion of a circuit device. The motor shaft is designed to be secured to the other portion of the circuit device and to rotate or oscillate in a controllable manner. When a failure condition of the circuit device is detected, means for reducing torque applied to the circuit device are activated. Means for reducing torque include the use of mechanical mechanisms such as springs and flexible clamping material, as well as torque limiting shafts. Means for reducing torque further include the use of electromechanical mechanisms including measuring devices such as strain gauges, thermocouples, ammeters, ohmmeters, and voltmeters. Means for reducing torque further yet include systems to interpret feedback from measuring devices and automatically adjust the applied torque. In some instances, the means for reducing torque will cause a cessation of the application of torque.

Certain other aspects of the invention are directed to encoding and decoding equipment and circuits constructed and arranged to operate according to the above methodology.

The above summary is not intended to characterize each embodiment of the present invention. Other aspects of the present invention will become apparent upon review of the figures and corresponding "Detailed Description".

BRIEF DESCRIPTION OF THE DRAWINGS

Various aspects and advantages of the present invention will become apparent upon reading the following detailed description of various embodiments and upon reference to the drawings in which.

Figure 1:
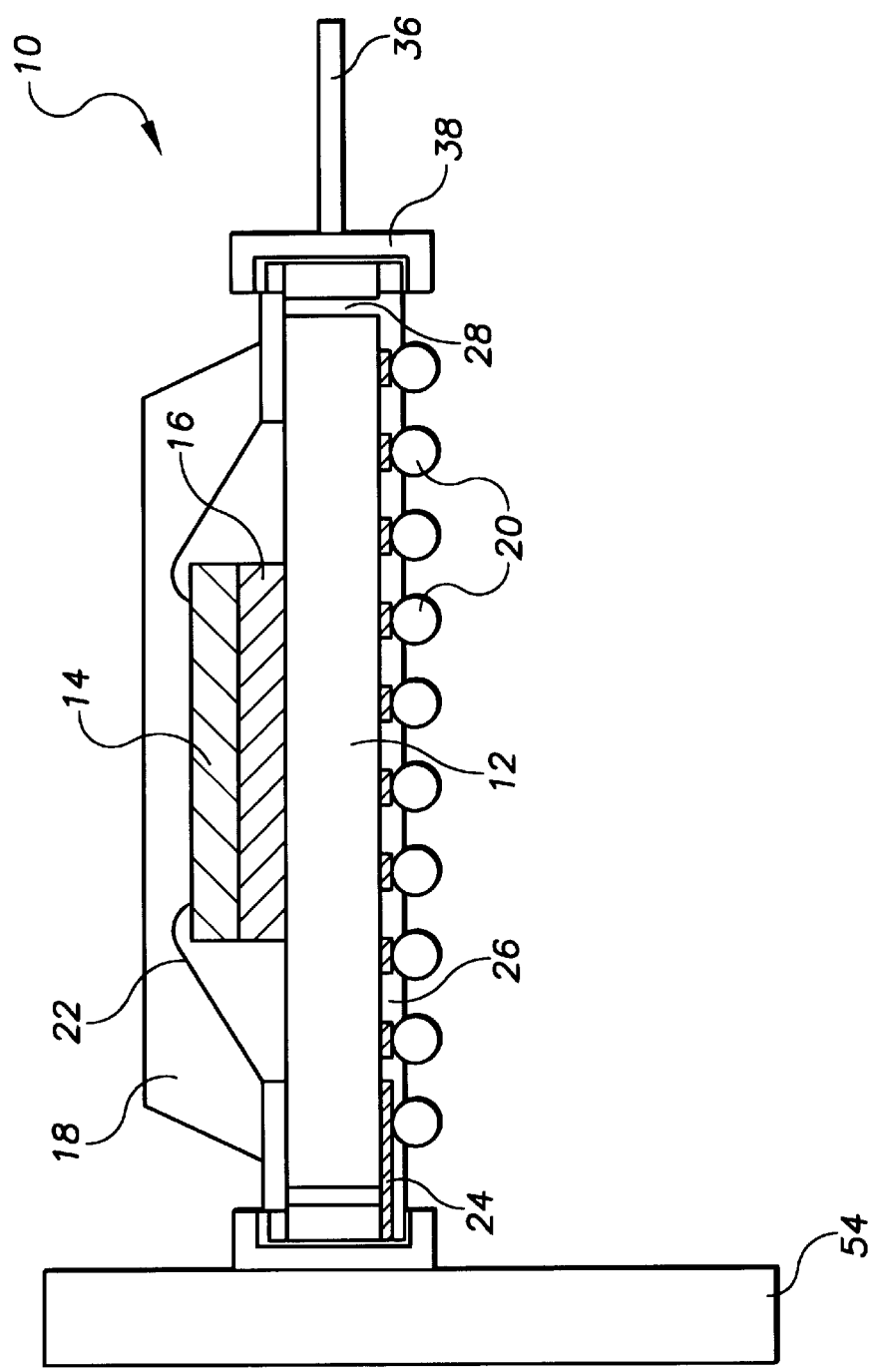
FIG. 1 illustrates a cross-sectional view of an assembly, according to an example embodiment of the present invention, including an over-molded PBGA package, a clamping mechanism for securing one side of the over-molded PBGA package and a motor shaft attached to another side of the over-molded PBGA package.

While the invention is amenable to various modifications and alternative forms, specifics thereof have been shown by way of example in the drawings and will be described in detail. It should be understood, however, that the intention is not to limit the invention to the particular embodiment described. On the contrary, the invention is to cover all modifications, equivalents, and alternatives falling within the spirit and scope of the invention as defined by the appended claims.

DETAILED DESCRIPTION

The present invention is applicable to a variety of circuit devices that require or benefit from the satisfaction of certain integrity standards. The present invention has been found to be particularly advantageous for use in testing the integrity of circuit devices such as plastic ball grid array (PBGA) packages, printed circuit boards (PCBs), and packages mounted on PCBs, such as PBGA packages, ceramic BGA packages, PQFP surface mount devices, and the like, hereinafter referred to collectively as circuit devices.

FIG. 1 illustrates a cross sectional view of a circuit device 10, such as a PGBA or PCB. It should be emphasized, however, that the scope of the invention is not limited to such specific structures, but can also be utilized in other applications requiring torque to be applied to a workpiece for testing or processing. As illustrated, the circuit device includes a substrate 12, upon which is mounted a semiconductor chip 14. The substrate 12 is typically a laminate of FR4 fiberglass or BT resin coating glass reinforcement material. Between the substrate 12 and semi-conductor chip 14 is a die attach 16. A solder mask 26 is disposed on the circuit device 10. Often, the entire circuit device will be overmolded or glob top 18 to provide stability. Additional electronic components, such as circuitry, connectors, switches, transistors, and chips, may also be disposed on the substrate 12. Some form of electrical connection between the various components, bonding pads and terminals, for example, must necessarily be present. Typically, these connections will exist in the form of solder joints. For the circuit device to function properly, the interfaces between all components must have structural and electrical integrity.

Figure 4:
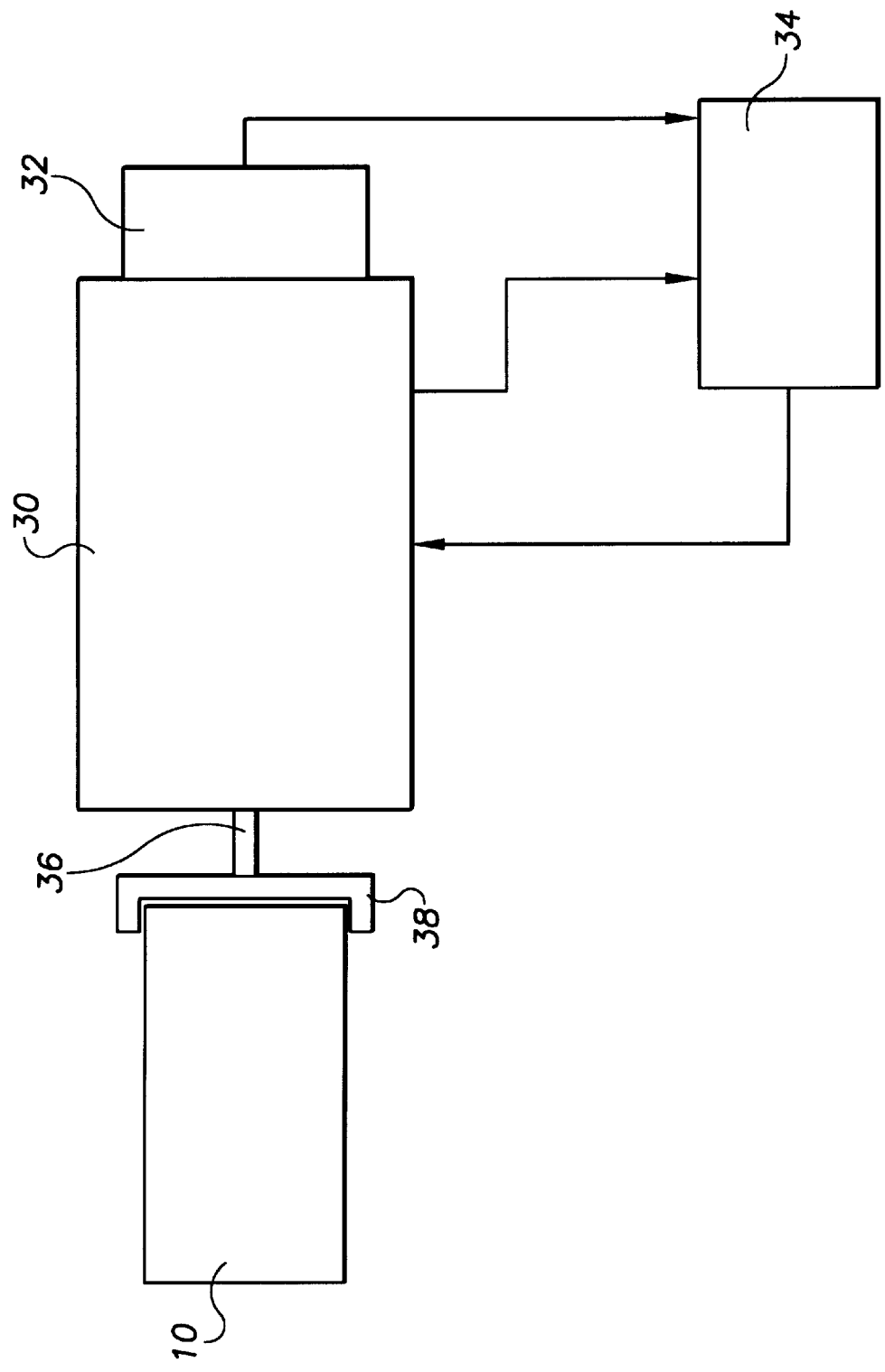
FIG. 4 illustrates a schematic view of an embodiment of the present invention, including a PCB, connected by a shaft to a servo motor, which is controlled by a central processing unit.

One end of the circuit device 10 is affixed to a clamping device 54, for securely holding the circuit device 10 during testing. As best shown in FIG. 4, the other end of the circuit device 10 is temporarily affixed to a bracket 38. The bracket 38 is fixedly attached to a shaft 36, which is fixedly attached to a servo motor 30. A position detector 32 is attached to the servo motor 30, for precisely directing the position of the servo motor in response to commands received from a central processing unit (CPU) 34. A means for indicating device failure is used, and such means include energizing the circuit during testing and other methods such as the use of electromagnetic radiation, a photo-emission microscope, or a combination thereof.

Figure 2:
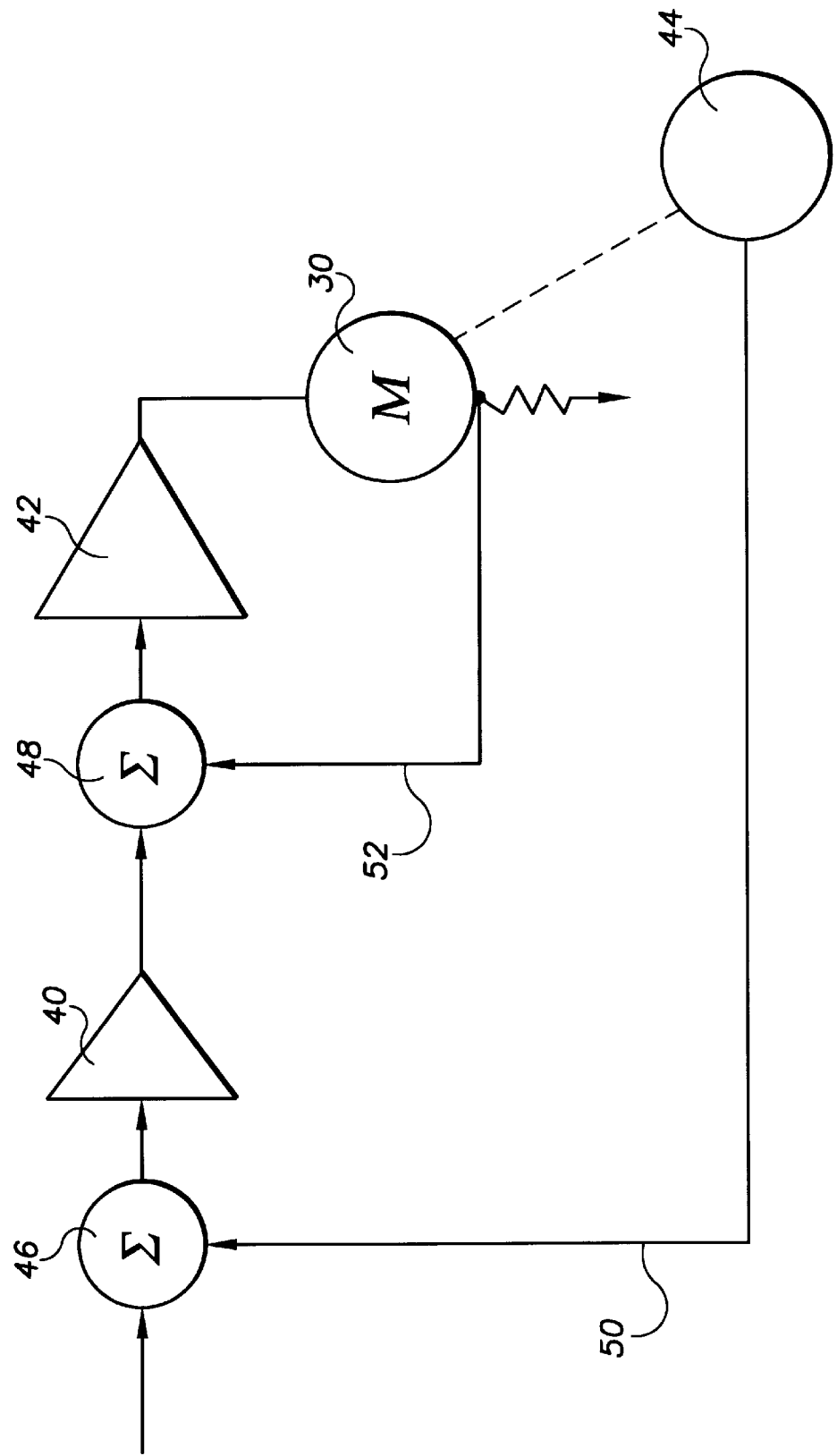
FIG. 2 illustrates a circuit diagram for controlling the assembly of FIG. 1, according to another example embodiment of the present invention.

FIG. 2 illustrates a circuit diagram as used for controlling an embodiment of the present invention. A servo motor 30 is affixed to the circuit device 10 (not shown) to be tested. The servo motor 30 is controlled by a combination of inputs from a controller 34, as in FIG. 4, which is preset by the operator, and feedback from a position sensor 44, which monitors the performance of the servo motor 30. The controller input and the position feedback signal 50 are combined by the position command circuit 46. The combined signal is then amplified by the amplifier 40. Following amplification of the signal from the amplifier 40, the signal is combined with current feedback 52 received from the servo motor 30 by the current command circuit 48. The signal from the current command circuit 48 is amplified by the power amplifier 42, which is fed to the servo motor 30, to precisely control the position and forces exerted on the circuit device 10 (not shown). Destructive stress levels are determined during testing, using methods for indicating device failure. Examples of device failure may include failure related to solder joint fatigue and package interface adhesion. When the destructive stress level is reached, the amount of torque exerted by the servo motor 30 on the circuit device 10 is reduced, and in most cases terminated.

Figure 3:
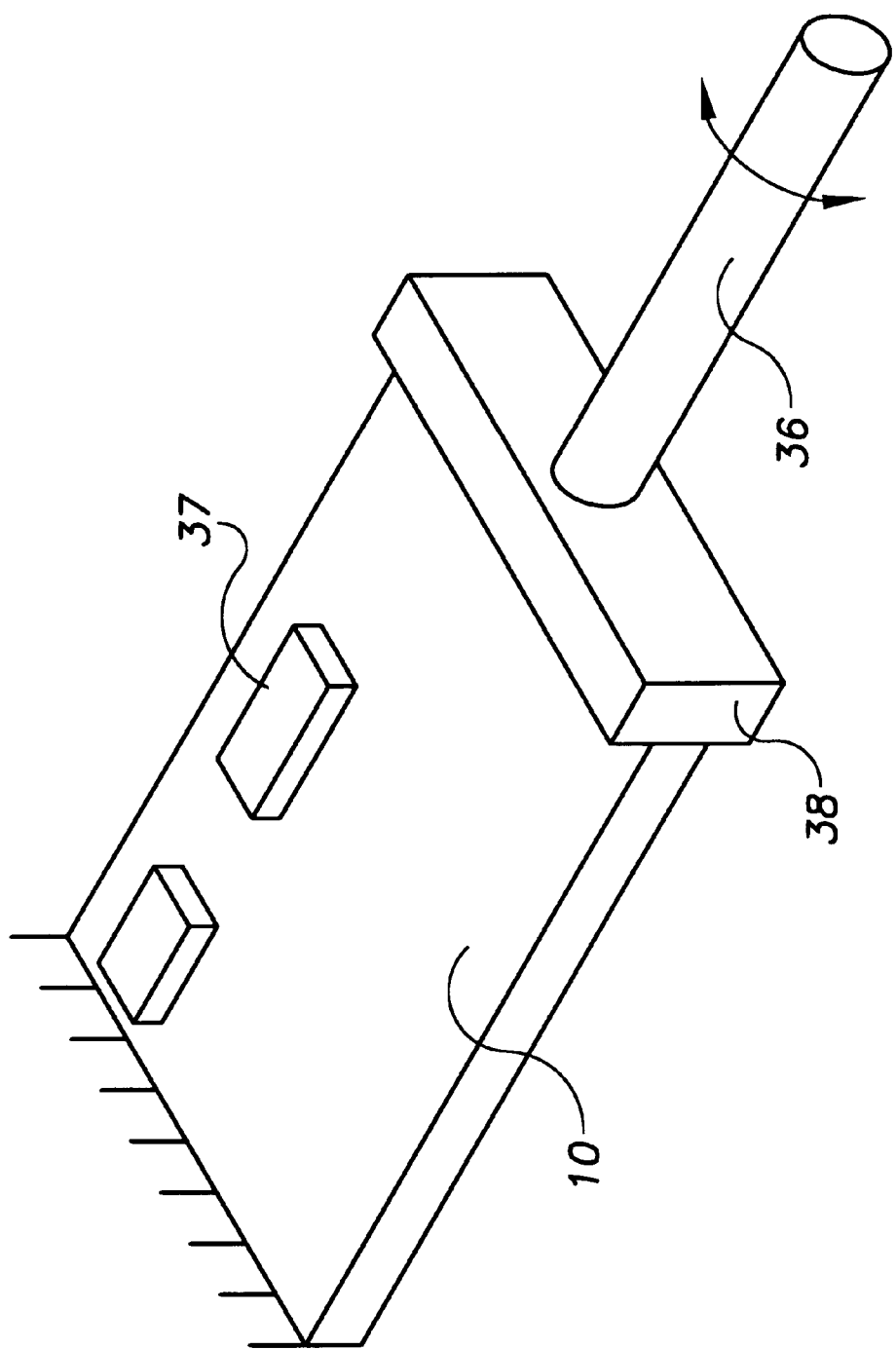
FIG. 3 illustrates a simplified, perspective view of an assembly, according to another example embodiment of the present invention.

FIG. 3 shows a simplified, perspective view of an embodiment of the present invention as testing is occurring. The circuit device 10 is secured sufficiently to prevent twisting at one end while the other end is mounted in a bracket 38. A rotatable shaft 36 is attached to bracket 38 to apply torque to the circuit device 10 during testing. The other end of shaft 36 is attached to a servo motor 30 (not shown), which is precisely controlled so as to be able to accurately determine the mechanical strength of the circuit device 10, as well as the amount of force required to cause failure of the circuit device 10. Optionally, one or more surface mount components 37 may be attached to circuit device 10.

In one particular embodiment, the present invention is directed to testing a PCB by applying a rotation to the rotatable shaft of about a few tenths of a degree per lateral inch of the PCB.

In another particular embodiment, the present invention is directed to testing a PBGA package by applying a rotation to the rotatable shaft of about 5 to 10 degrees per PBGA package.

In still another particular embodiment, the present invention is directed to testing a PCB by applying a torque of about 10–12 inch-pounds.

In yet another particular embodiment, the present invention is directed to testing a PBGA package by applying a torque of about 80–100 inch-pounds.

The various embodiments described above are provided by way of illustration only and should not be construed to limit the invention. Those skilled in the art will readily recognize various modifications and changes which may be made to the present invention. For example, various different types of mechanisms can be used to secure the opposing portions of the illustrated circuit devices under evaluation. Such mechanisms include vices and elastic bands over one side of the device, and permanent or temporary adhesion materials such as tape and glue. In another example, the values of applied torque and angular displacement used for testing can be varied to suit the requirements of various board dimensions and the strength of the board material used. These modifications do not depart from the teaching, or the true spirit and scope, of the present invention. The invention is set forth in the following claims.

What is claimed is:

1. A method for evaluating the integrity of a circuit device, the method comprising:

stabilizing a portion of the circuit device relative to another portion of the circuit device;

providing a controllable servo motor having a shaft;

providing a servo-controller having a feedback circuit including a position command circuit and a position sensor that monitors the performance of the servo motor, wherein the servo-controller is constructed and arranged to cause the servo motor to controllably rotate the shaft;

securing the shaft to the other portion of the circuit device;

obtaining position data with the position sensor and sending a position feedback signal to the position command circuit;

combining the position feedback signal with a signal from a controller input;

using the servo-controller and the combined signals to provide a torque to the circuit with the servo-controller; and at least reducing the torque in response to detecting a failure condition of the circuit device.

2. A method, according to claim 1, wherein the circuit device includes a printed circuit board and the step of stabilizing a portion of the circuit device relative to another portion of the circuit device includes stabilizing the printed circuit board.

3. A method, according to claim 2, wherein the failure condition is an electrical connection failure.

4. A method, according to claim 2, wherein the step of using the servo-controller includes applying an angular displacement.

5. A method, according to claim 4, wherein the step of using the servo-controller includes applying cyclic stress.

6. A method according to claim 2, wherein the step of using the servo-controller includes applying cyclic stress.

7. A method, according to claim 2, wherein the failure condition is an electrical connection failure and the step of using the servo-controller includes applying cyclic stress as well as an angular displacement of about a few tenths of a degree.

8. A method, according to claim 1, wherein the circuit device includes a PBGA package and the step of stabilizing a portion of the circuit device relative to another portion of the circuit device includes stabilizing the PBGA package.

9. A method, according to claim 8, wherein the failure condition is a failure in the PBGA package.

10. A method, according to claim 8, wherein the circuit device includes a BGA package, and wherein the failure condition is a failure in the BGA package.

11. A method, according to claim 8, wherein the circuit device includes a PQFP package, and wherein the failure condition is a failure in the PQFP package.

12. A method, according to claim 8, wherein the step of using the servo-controller includes applying a torque of about 80–100 inch-pounds.

13. A method, according to claim 8, wherein the step of using the servo-controller includes applying an angular displacement of about a few tenths of a degree to test for field reliability.

14. A method, according to claim 8, wherein the step of using the servo-controller includes applying an angular displacement of about 5–10 degrees.

15. A method, according to claim 2, wherein the failure condition is a package failure and the step of using the servo-controller includes applying a torque of about 80–100 inch-pounds as well as an angular displacement of about 5–10 degrees.

16. A method, according to claim 1, wherein at least reducing the torque includes ceasing application of the torque.

17. An arrangement for evaluating the integrity of a circuit device, the arrangement comprising:

means for stabilizing a portion of the circuit device relative to another portion of the circuit device;

an assembly including a controllable motor shaft and a servo-controller having a feedback circuit including a position sensor and a position command circuit, wherein the servo-controller is constructed and arranged to cause the motor to controllably rotate the shaft;

means for securing the shaft to the other portion of the circuit device;

means for sending a position feedback signal to the position command circuit and combining the position feedback signal with a signal from a controller input;

means for using the servo-controller and the combined signals to torque the circuit device; and means for at least reducing the torque in response to detecting a failure condition of the circuit device.

18. An arrangement, according to claim 17, wherein said means for at least reducing the torque includes means for ceasing application of the torque.

19. An arrangement, according to claim 17, wherein said means for at least reducing the torque includes means for controlling application of the torque at different torque magnitudes.

20. A method, according to claim 1, further comprising obtaining a current feedback signal from the servo motor and combining the current feedback signal with the combined position feedback signal and controller input signal, wherein using the servo-controller and the combined signals to provide a torque includes using the current feedback signal.

* * * * *